United States Patent [19]

Falk

[11] 4,098,811

[45] Jul. 4, 1978

[54] PERFLUOROALKYLTHIOAMIDO AMINE AND AMMONIUM COMPOUNDS

[75] Inventor: Robert A. Falk, New City, N.Y.

[73] Assignee: CIBA-GEIGY Corporation, Ardsley, N.Y.

[21] Appl. No.: 747,113

[22] Filed: Dec. 2, 1976

[51] Int. Cl.[2] .......................................... C07C 141/04

[52] U.S. Cl. ........................... 260/459 A; 260/458 F; 260/458 C; 260/459 R; 260/501.12; 260/561 A; 260/561 HL; 260/561 S; 544/386; 544/158

[58] Field of Search ........ 260/561 S, 561 A, 561 HL, 260/501.12, 458 F, 458 E, 459 A, 459 C

[56] References Cited

U.S. PATENT DOCUMENTS

| | | | |
|---|---|---|---|
| 2,764,602 | 9/1956 | Ahlbrecht | 260/561 HL |
| 3,093,146 | 6/1963 | Kalopissis et al. | 260/561 S |
| 3,172,910 | 3/1965 | Brace | 260/561 S |
| 3,547,995 | 12/1970 | Bartlett | 260/561 HL |
| 3,555,089 | 1/1971 | Bartlett | 260/561 HL |
| 3,576,019 | 4/1971 | Sweeney et al. | 260/561 HL |
| 3,697,564 | 10/1972 | Anello et al. | 260/561 HL |
| 3,940,435 | 2/1976 | Hiestand | 260/561 S |

*Primary Examiner*—Arthur P. Demers

*Attorney, Agent, or Firm*—Edward McC. Roberts; Michael W. Glynn; Prabodh I. Almaula

[57] ABSTRACT

The perfluoroalkylthio amidoalkyl amine or ammonium compounds having the structures

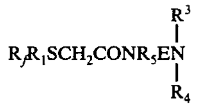

and

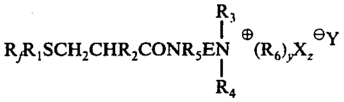

where $R_f$ is a perfluoroalkyl, $R_1$ is alkylene or alkylene oxy or amino alkylene, $R_2$ is hydrogen or alkyl, $R_3$ and $R_4$ are independently alkyl or together form a heterocyclic ring, $R_5$ is hydrogen or alkyl, $R_6$ is hydrogen, oxide, alkyl or substituted alkyl, E is alkylene or polyoxyalkylene, X is an anion, $y$ is 1 or 2 and $z$ is 0 or 1, which can be prepared by the base-catalyzed addition of a perfluoroalkylthiol to an $\alpha,\beta$-unsaturated amide. These compounds are useful as surfactants.

9 Claims, No Drawings

PERFLUOROALKYLTHIOAMIDO AMINE AND AMMONIUM COMPOUNDS

BACKGROUND OF THE INVENTION

Esters of perfluoroalkyl terminated alkylene thioalkanoic acids and their derivatives have been described in the prior art (U.S. Pat. No. 3,759,981). These surfactants suffer from a marked unstability of the ester function towards hydrolysis and consequently are of little practical use.

The amides of this invention, however, are very stable to hydrolysis and therefore find many uses as surfactants and wetting agents.

Perfluoroalkylthioamide amine and ammonium compounds of this invention are useful as surface active agents or as surface treating and coating agents. The novel compounds are obtained by the addition of a perfluoroalkylthiol to an amide of an $\alpha$, $\beta$-unsaturated acid. The cationic and amphoteric salts of these compounds are also described.

The compounds of this invention can be represented by the formulae

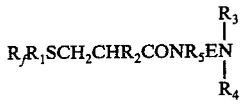

I and

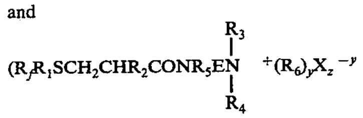

where $R_f$ is straight or branched chain perfluoroalkyl of 1 to 18 carbon atoms or said perfluoroalkyl substituted by perfluoroalkoxy of 2 to 6 atoms;

$R_1$ is branched or straight chain alkylene of 1 to 12 carbon atoms; alkylenethioalkylene of 2 to 12 carbon atoms; alkyleneoxyalkylene of 2 to 12 carbon atoms; or alkyleneiminoalkylene of 2 to 12 carbon atoms where the nitrogen atom contains as a third substituent hydrogen or alkyl of 1 to 6 carbon atoms;

$R_2$ is hydrogen or straight or branched chain alkyl of 1 to 6 carbon atoms;

$R_3$ and $R_4$ each is independently straight or branched chain alkyl of 1 to 22 carbon atoms; or $R_3$ and $R_4$, together with the nitrogen to which they are bonded, form a heterocyclic ring:

$R_5$ is hydrogen or straight or branched chain alkyl of 1 to 6 carbon atoms.

$R_6$ is hydrogen; oxide; or straight or branched chain alkyl of 1 to 22 carbon atoms that may be substituted with 1 or 2 hydroxyl groups, a free carboxylic acid group, or an anionic function selected from sulfonate, sulfate, or carboxylate;

E is a straight or branched chain alkylene of 1 to 12 carbon atoms; or alkylene (polyoxyalkylene) of formula $$C_mH_{2m}(OC_kH_{2k})_r$$

where

*m* is an integer of 1 to 12;

*k* is an integer of 2 to 6;

*r* is an integer of 1 to 40;

or E together with the two nitrogen atoms and $R_3$ forms a piperazine ring having the structure

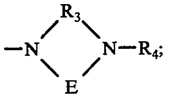

X is an anion selected from the group consisting of Br, Cl, I, acetate, phosphate, sulfate, methosulfate or ethosulfate;

*y* is 1 or 2, depending on the valence of X; and

*z* is 0 or 1, with the proviso that when *z* is 0, *y* is 1 and $R_6$ must be oxygen or an anionic function; if *z* is 1, $R_6$ may not be oxygen.

Preferred compounds are those where $R_f$ is straight or branched chain perfluoroalkyl of 6 to 12 carbon atoms or said perfluoroalkyl substituted by perfluoroalkoxy of 2 to 6 carbon atoms;

$R_1$ is branched or straight chain alkylene of 2 to 8 carbon atoms; alkylenethioalkylene of 2 to 8 carbon atoms: alkyleneoxyalkylene of 2 to 8 carbon atoms; or alkyleneiminoalkylene of 2 to 8 carbon atoms where the nitrogen atom contains hydrogen or methyl as a third substituent;

$R_2$ is hydrogen or methyl;

$R_3$ and $R_4$ each is independently straight chain alkyl of 1 to 12 carbon atoms; or $R_3$ and $R_4$, together with the nitrogen to which they are bonded form a heterocyclic ring;

$R_5$ is hydrogen;

$R_6$ is hydrogen; oxide; or straight chain alkyl of 1 to 3 carbon atoms that may also contain 1 hydroxyl group, a free carboxylic acid group, or an anionic function selected from sulfonate, sulfate, of carboxylate;

E is a straight chain alkylene of 2 or 3 carbon atoms; or alkylene (polyoxyalkylene) of formula $$C_mH_{2m}(OC_kH_{2k})_r$$

where

*m* is an integer from 1 to 4

*k* is an integer from 2 to 4

*r* is an integer from 1 to 20, or E together with the two nitrogen atoms and $R_3$ forms a piperazine ring;

X is an anion selected from the group consisting of Br, Cl, I, acetate, phosphate, sulfate, methosulfate or ethosulfate;

*y* is an integer equal to the valence of X;

*z* is 0 or 1, with the proviso that when *z* is zero, *y* is 1, and $R_6$ must be oxygen or an anionic function; when *z* is 1, $R_6$ may not be oxygen.

The novel $R_f$-surfactants described herein can be obtained either:

a. directly by the base-catalyzed addition of a perfluoroalkylthiol of formula $$R_fR_1SH$$

to an $\alpha,\beta$-unsaturated amide of formula $$CH_2{=}CR_2CONR_5ENR_3R_4$$

where $R_f$, $R_1$, $R_2$, $R_3$, $R_4$, $R_5$ and E are defined above, or b. indirectly by the further reaction of the above products with such quaternizing agents as alkyl halides, dialkyl sulfates and the like to yield cationic surfactants or with inorganic acids or organic acids to form salts, or by reaction with such alkylation reagents as chloroacetic acid, sodium chloroacetate, propane sultone, propiolactone and the like, to yield amphoteric surfactants. Amine oxide derivatives wherein $R_6$ is oxygen are prepared by treatment with hydrogen peroxide at about 0° to 50° C.

One group of preferred compounds has the formula $R_fCH_2CH_2SCH_2CH(CH_3)CONH(CH_2)_3N(CH_3)_2$ and the corresponding ammonium derivatives $[(R_fCH_2CH_2SCH_2CH(CH_3)CONH(CH_2)_3N(^+CH_3)\text{-}_2C_2H_5)]C_2H_5SO_4^-$ and $R_fCH_2CH_2SCH_2CH(CH_3)CONH(CH_2)_3N^+(CH_3)_2.CH_2CO_2^-$ where $R_f$ is perfluoroalkyl of 6 to 12 carbon atoms or perfluoroalkoxyperfluoroalkyl of 4 to 12 carbon atoms, and especially where $R_f$ if $(CF_3)_2CFO(CH_2CF_2)_y$ where $y$ is an integer from 1 to 6.

In one embodiment, the $\alpha,\beta$-unsaturated amide has the formula $CH_2{=}CR_2CONHENR_3R_4$ where E is a straight chain alkylene of 2 to 3 carbon atoms, and $R_3$ and $R_4$ are each independently straight chain alkyl of 1 to 3 carbon atoms; or $R_3$ and $R_4$ together with nitrogen forms a morpholinium group. In a preferred embodiment $R_3$ and $R_4$ are both methyl or ethyl groups.

The amides wherein $R_2$ is hydrogen or methyl, E is ethyl or propyl and $R_3$ and $R_4$ are methyl or ethyl are commercially available but are not as common as (meth)acrylate esters. Canadian Pat. Nos. 595,642 and 583,352 disclose the preparation of some of these amides.

The $\alpha,\beta$-unsaturated amide may also be employed as a cationic or amphoteric salt, e.g., $CH_2{=}CR_2CONHENR_3R_4(R_6)_y{}^+X_z{}^{-y}$ wherein the substituents are as heretofor defined.

In one embodiment, $R_6$ is methyl and X is methosulfate and in another embodiment, $R_6$ is $-CH_2CH_2CO_2^-$.

Cationic and amphoteric derivatives are most usually made, however, by subsequent alkylation of $\alpha,\beta$-unsaturated amide adducts.

Perfluoroalkyl thiols useful herein are well documented in the prior art. For example, thiols of the formula $R_fR'{-}SH$ have been described in a number of U.S. Patents including U.S. Pat. Nos. 2,894,991; 2,961,470; 2,965,677; 3,088,849; 3,172,190; 3,544,663; and 3,655,732.

Thus, U.S. Pat. No. 3,655,732 discloses mercaptans of formula $R_f{-}R'{-}SH$ where R' is alkylene of 1 to 16 carbon atoms and $R_f$ is perfluoroalkyl and teaches that halides of formula $R_f{-}R'$-hal are well known. Reaction $R_fI$ with ethylene under free-radical conditions gives $R_f(CH_2CH_2)_aI$ as is further taught in U.S. Pat. Nos. 3,088,849; 3,145,222; 2,965,659 and 2,972,638.

U.S. Pat. No. 3,655,732 further discloses compounds of formula $R_f{-}R'{-}X{-}R''{-}SH$ where R' and R'' are alkylene of 1 to 16 carbon atoms, with the sum of carbon atoms of R' and R'' being no greater than 25; $R_f$ is perfluoroalkyl of 4 through 14 carbon atoms and X is —S— or —NR''' where R''' is hydrogen or alkyl of 1 through 4 carbon atoms.

U.S. Pat. No. 3,544,663 teaches that the mercaptan $R_fCH_2CH_2SH$ where $R_f$ is perfluoroalkyl of 5 to 13 carbon atoms, can be prepared by reacting the perfluoroalkylalkylene iodide with thiourea or by adding $H_2S$ to a perfluoroalkyl substituted ethylene ($R_f{-}CH{=}CH_2$), which in turn can be prepared by dehydrohalogenation of the halide $R_f{-}CH_2CH_2$—hal.

The reaction of the iodide $R_f{-}R'{-}I$ with thiourea followed by hydrolysis to obtain the mercaptan $R_f{-}R'{-}SH$ is the preferred synthetic route. The reaction is applicable to both linear and branched chain iodides. U.S. Pat. No. 3,514,487 described perfluoroalkoxyalkyl iodides of general formula $(CF_3)_2CFOCF_2CF_2(CH_2CH_2)_mI$ where $m$ is 1-3.

Particularly preferred herein are the thiols of formula $R_fCH_2CH_2SH$ where $R_f$ is perfluoroalkyl of 6 to 12 carbon atoms. These $R_f$-thiols can be prepared from $R_fCH_2CH_2I$ and thiourea in very high yields.

The quaternary ammonium derivatives (cationic and amphoteric salts) of formula II can be prepared from the compounds of formula I by methods well known to the art (e.g., U.S. Pat. No. 2,759,019).

The addition of a perfluoroalkylthiol of formula $R_fR_1SH$ to an $\alpha,\beta$-unsaturated amide is a base-catalyzed reaction (Hauben-Weyl, Methoden der Organischen Chemie, Vol. 9, pp. 123-6). Since the amino group containing compounds are themselves basic, it is generally not necessary to use a catalyst for the Michael type addition. The addition reaction can be carried out neat or in a solvent employing reaction temperatures ranging from 10° to 150° C and reaction time from minutes to 18 hours. Suitable solvents are such in which the reactants are soluble at reaction temperatures and include aliphatic or aromatic hydrocarbons such as heptane, benzene, toluene, etc.; chlorinated or fluorinated aliphatic or aromatic hydrocarbons such as methylene chloride, chloroform, methyl chloroform, carbon tetrachloride, trichloroethylene, perchloroethylene, Freon's such as 1,1,2-trifluoro-1,2,2-trichloroethane, etc., chlorobenzene, benzotrifluoride or hexafluoroxylene, ketones, esters and ethers such as acetone, methyl isobutyl ketone, ethyl acetate and higher homologs, dialkyl ethers, tetrahydrofuran, ethylene glycol monomethyl or monoethyl ether, ethylene glycol dimethyl or diethyl ether, and acetonitrile.

If possible it is preferred to carry out the addition reaction in bulk.

Such fluorochemical surfactants are useful to improve or impart properties such as: wetting, penetration, spreading, leveling, foam stability, flow properties, emulsification, dispersion, and oil and water repellency. Based on these unique properties are numerous applications, some of which follow. Although applications are suggested for a particular use area, the general applicability of each concept is inferred for other applications.

PLASTICS AND RUBBER INDUSTRY

Emulsifying agent for polymerization, particularly fluoromonomers

As a latex stabilizer

To aid in the preparation of agglomerates of powdered fluorocarbon polymers

In synergistic mixtures with hydrocarbon surfactants to wet low energy surfaces including natural and synthetic rubbers, resins, plastics As an adjuvant for foam applications and as foaming agents to aid in leak detection As a foam additive to control spreacing, crawling, edge buildup As mound release agents, for silicones, etc.

In refractory processes

As an anti-mist film former

Additive for elimination of trapped air in plastic laminates

Wetting agent for resin molds for definition, strength

Hot-melt additive for oil and grease repellency

Resin additive for improved wetting of and bonding with fillers

Flow modifier for extruding hot melts: spreading, uniformity, anti-cratering

Adjuvant for resin etchant

Mold release agent, demoulding agent

Retarder for plasticizer migration or evaporation

Internal antistatic agent for polyolefins

Antiblocking agent for polyolefins

PETROLEUM INDUSTRY

Wetting assistant for oil well treatments, drilling muds

As a film evaporation inhibitor for gasoline, jet fuel, solvents, hydrocarbons

Lubricating, cutting oil improver, to improve penetration times

In extreme pressure EP lubricants

Oil spill collecting agent

Additive to improve tertiary oil well recovery

TEXTILE AND LEATHER INDUSTRIES

Soil release and soil proofing agent

Oil/water repellent textile and leather treatment

Wetting agent to improve coverage and penetration of pores of substrates

Anti-foaming agent in textile treatment baths

Wetting agent for finish-on-yarn uniformity

Penetrating agent for finishes on tow, heavy denier fibers

Emulsifying agent/lubricant/ for fiber finishes

Cleaner/metal treating agent for polymerization equipment

Flow modifier for spinning of hot melts, solutions

Additive for fabric finishes for spreading, uniformity

Wetting agent for dyeing

Penetration aid for bleaches

Wetting agent for binder in nonwoven fabrics

PAINT, PIGMENT AND FINISHING INDUSTRIES

Leveling, anti-catering adjuvant for finishes and paints

Adjuvant for control of soiling

Agent to control differential evaporation of solvents

Leveling agent for floor waxes

Adjuvant for waxes to improve oil and water repellency

Adhesion improver for oily or greasy surfaces

To combat pigment flotation problems

Improver for automotive finishes, based on water-based coatings in which the pigments are rendered non-reactive Pigment grinding aid to promote wetting, dispersion, color development Foam generator substance for the application of dyes, inks Electrolytic conversion coatings

MINING AND METALWORKING INDUSTRIES

In cleaning agents for property improvement

Additive for solvent cleaning

Additive for metal pickling baths to increase bath life and acid runoff

Additive for chrome electroplating: surface tension reduction, foaming

Additive for soldering flux, especially for electronic circuitry

Protective agent for coatings (tarnish resistance, grease repellency)

Corrosion inhibitor

Additive for etchant solution for improved definition

Plastic preplate and silicon etchant technology

In soldering flux for microelectronics to reduce foaming

In chemical roughing agent solutions, prior to galvanization

As a colloidal dispersion aid for magnetic solids

Protective coatings for aluminum and as an anti-blocking agent

Wetting agent for leaching copper ores and as a fresh flotation agent

To promote ore wetting and quicker breaking of the protective oxide layer

PHARMACEUTICAL INDUSTRY

Improve the properties and penetration of antimicrobial agents

Improve the properties of biochemicals, biocides, algicides, bacteriocides, and bacteriostats Improve the strength, homogeneity, and reduce the permeability of encapsulated materials Emulsify fluorochemical blood substitutes

AGRICULTURE AND FORESTRY

Wetting agent for herbicides, fungicides, weed killers, hormone growth regulators, parasiticides, insecticides, germicides, bactericides, nematocides, microbiocides, defolients and fertilizers As an ingredient in chemosterilents, insect repellents and toxicants For wettable powder pesticides and chemical powders Corrosion inhibitor for chemical applicators Wetting agent for foliage Wetting additive for live stock dips, or to wet sheep skins during desalination Wetting adjuvant for manufacture of plywood veneer Penetrant for preservative impregnation Pulping aid For cleaning tubes in paper making, dyeing Grease/oil repellents for paper

FIRE FIGHTING

Wetting agent for fighting forest fires

Ingredient of AFF, aqueous film forming extinguishing agents
Component of fluoroprotein foams
Additives to dry chemical extinguishing agents
Agent in aerosol-type extinguishers
Wetting agent for sprinkler water

AUTOMOTIVE BUILDING MAINTENANCE AND CLEANING

Wetting agent for cleaning compositions
Additive for alkaline cleaners
Glass cleaner
Wetting agent for automobile waxes
Adjuvant to improve oil/water repellency of wax
Lubricant/corrosion inhibitor for antifreeze
Rinse-aid for car washes
In dry cleaning compositions and solvent cleaners, for water displacement and foaming. May improve soil suspension and decrease redeposition
Foaming agents for pipe cleaning
Anti-mist film foamer for glass and plastics
In foams for dust suppression
For acidic concrete cleaners
Bubble foamer for air tracing, in ventilating systems

HOUSEHOLD, COSMETIC AND PERSONAL PRODUCTS

Rinse-aid for dishwashing
Liquid polishing compositions
Floor polish leveling agent
Additive for alkaline oven cleaners
Synergistic improver for disinfectants
Carpet cleaners
Synergistic wetting agent in detergent formulations
Additive for protective coatings on metals (tarnish resistance, grease resistance)
Gloss and antistatic improver
Hair shampoo ingredient
Shaving form ingredient
Oil and water repellent cosmetic powders ingredient
Ingredient of lotions or creams for skin or hair
Ingredient of skin protection creams

PHOTOGRAPHY AND GRAPHIC ARTS

Printing ink additive for ink flow and leveling, both aqueous and solvent based
Wetting agent for writing inks
To combat pigment flooding and flotation in printing inks
To form ink repellent surfaces for waterless lithoplates, or electrographic coatings
Prevent reticulation of gelatin layers and improve uniformity
Assist in film drying
Improve film coatings and reduce "contraction flecks"
Wetting, leveling, anti-cratering assist agent
Surfactant for developer solutions
Photoemulsion stabilizer
Prevent photo-lubricant acclomeration
Coating aid in the preparation of multiple layer film elements
Antistatic wetting agent for film coatings
Antifogging agent for films
Bonding agent for fillers and fluoropolymer films
In coatings for nematic liquid crystal cells

EXAMPLE 1

N-(3-Dimethylaminopropyl)-2-methyl-3-(1,1,2,-tetrahydroperfluorodecanethio)-propionamide $C_8F_{17}CH_2CH_2SCH_2CH(CH_3)CONHCH_2CH_2CH_2N(CH_3)_2$ 1,1,2,2-Tetrahydroperfluorodecanethiol (12.04 g, 0.025 mole), N-(3-dimethylaminopropyl)methacrylamide (3.88 g, 0.023 mole), and benzyltrimethylammonium hydroxide in methanol (4 drops) were heated overnight at 70° C. The resultant mixture was stripped of volatiles and distilled at 150°/≠0.1 mm Hg to yield 11.7 g of pale-yellow liquid (78.1% theory) which subsequently crystallized to a solid, m.p. 47°-50° C. NMR showed proton resonances at δ1.05, 3 protons, CH $CH_3$; δ1.55, 2 protons, $NHCH_2\underline{CH_2}CH_2N(CH_3)_2$; δ2.10, 6 protons, 2 × $N\underline{CH_3}$; δ2.00–δ2.80, 10 protons, $CF_2\underline{CH_2CH_2}S\underline{CH_2}$ + $NH\underline{CH_2}CH_2\underline{CH_2}N$; δ3.05; 1 proton, $\underline{CH}(CH_3)CO$; δ7.50, 1 proton, $N\underline{H}$.

Analysis for $C_{19}H_{23}F_{17}N_2OS$: Calc: C, 35.09; H, 3.56; F, 49.65; N, 4.31. Found: C, 35.02; H, 3.40; F, 49.71; N, 4.35.

EXAMPLE 2

3-[2-Methyl-3-(1,1,2,2-tetrahydroperfluorodecanethio) propionamido]propyltrimethylammonium iodide $C_8F_{17}CH_2CH_2SCH_2CH(CH_3)CONHCH_2CH_2CH_2N(CH_3)_3\ ^-I$ N-(3-Dimethylaminopropyl)-2-methyl-3-(1,1,2,2-tetrahydroperfluorodecanethio)-propionamide (0.83 g, 0.0013 mold), iodomethane (0.35 g, 0.0025 mole), and methanol (3 g) were heated together at 50° C for 3 hours. The resultant mixture was stripped of all volatiles to yield 1.0 g product (95.1% of theory) as a white powder. NMR showed proton resonances at δ1.23, 3, protons, $CH\underline{CH_3}$; δ3.32, 9 protons, $N^+$-$\underline{CH_3}$ × 3; δ2.00–3.83, 13 protons, $C_8F_{17}\underline{CH_2CH_2}S\underline{CH_2CH}(CH_3)CONH\underline{CH_2CH_2}CH_2$; δ7.55, 1 proton, $N\underline{H}$.

Analysis for $C_{20}H_{26}F_{17}IN_2OS$: Calc: C, 30.32; H, 3.31; F, 40.76; N, 3.54. Found: C, 30.39; H, 3.42; F, 41.04; N, 3.22.

EXAMPLE 3

N-(3-Dimethylamino)propyl-2-methyl-3-(1,1,2,2-tetrahydroperfluoroalkanethio)-propionamide $R_fCH_2CH_2SCH_2CH(CH_3)CONHCH_2CH_2CH_2N(CH_3)_2$ 1,1,2,2-Tetrahydroperfluoroalkanethiol[b] (11.72 g, 0.025 mole), N-(3-dimethylaminopropyl)methacrylamide (3.88 g, 0.023 mole), and benzyltrimethylammonium hydroxide in methanol (4 drops) were heated overnight at 70° C. The resultant mixture was stripped of volatiles to 140°/0.01 mm Hg to yield 12.5 g product (85.2% of theory) as a waxy yellow solid, pure by GLC.

[b] $R_f$ distribution $C_6$, $C_8$, $C_{10}$, $C_{12}$ — 40, 40, 13, 2

EXAMPLE 4

3-[2-methyl-3-(1,1,2,2-tetrahydroperfluorodecanethio)-propionamido]propyltrimethylammonium iodide

[b]$R_fCH_2CH_2SCH_2CH(CH_3)CONHCH_2CH_2CH_2N^+(CH_3)_3\ I^-$

N-(3-Dimethylaminopropyl)-2-methyl-3-(1,1,2,2-tetrahydroperfluoroalkanethio)propionamide (3.00 g, 0.0049 mole), iodomethane (1.38 g, 0.0097 mole), and methanol (12 g) were heated at 50° C for 5 hours. All volatiles were removed at 100°/0.05 mm Hg to yield 3.69 g product (100% theory), as a yellow solid.

$^{b}R_f$— see distribution in Example 3

EXAMPLE 5

An identical preparation to the above was carried out with an amide prepared as in Example 3 having an $R_f$-distribution $^{b}R_f$ as indicated in Table 2.

EXAMPLE 6

3-[2-methyl-3(1,1,2,2-tetrahydroperfluorodecanethio) propionamido]propyldimethylethylammonium ethyl sulfate $C_8F_{17}CH_2CH_2SCH_2CH(CH_3)CONHCH_2CH_2CH_2N(CH_3)_2CH_2CH_3\ CH_2CH_3SO_4^-$ N-(3-Dimethylaminopropyl)-2-methyl-3-(1,1,2,2-tetrahydroperfluorodecanethio)-propioamide (1.00 g, 0.0015 mole), diethylsulfate (0.24 g, 0.0015 mole), and methanol (4.85 g) were heated on a steam bath for 5 minutes and allowed to stand at room temperature overnight. The product was dried at 100°/.05 mm Hg, rinsed with cyclohexane and redried to yield 1.18 g product (95.2% of theory) as a clear gel NMR showed proton resonances at δ0.95 -δ1.40, 9 protons, $CH\underline{CH_3}$ and $NCH_2\underline{CH_3}$; δ1.85 2 protons, $NH\underline{CH_2}CH_2N^+$; δ2.20-2.90, 9 protons, $\underline{CH_2CH_2}S\underline{CH_2CH}(CH_3)CO$; δ3.00, 6 protons, 2 × $N^+\underline{CH_3}$; δ3.00-3.40, 6 protons, $\underline{CH_2}CH_2\underline{CH_2}N^+\underline{CH_2}$.

Analysis for $C_{23}H_{33}F_{17}N_2O_5S_2$: Calc: C, 34.33; H, 4.13; N, 3.48. Found: C, 32.40; H, 3.87; N, 3.51.

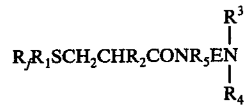

and

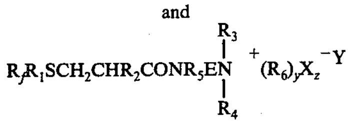

wherein $R_f$ is straight or branched chain perfluoroalkyl of 1 to 18 carbon atoms or said perfluoroalkyl substituted by perfluoroalkoxy of 2 to 6 atoms;

$R_1$ is branched or straight chain alkylene of 1 to 12 carbon atoms, alkylenethioalkylene of 2 to 12 carbon atoms, alkyleneoxyalkylene of 2 to 12 carbon atoms of alkyleneiminoalkylene of 2 to 12 carbon atoms where the nitrogen atom contains as a third substituent hydrogen of alkyl of 1 to 6 carbon atoms;

$R_2$ is hydrogen or straight or branched chain alkyl of 1 to 6 carbon atoms;

$R_3$ and $R_4$ each is independently straight or branched chain alkylyl of 1 to 22 carbon atoms;

$R_5$ is hydrogen or straight or branched chain alkyl of 1 to 6 carbon atoms, or $R_5$ is a covalent bond if a heterocyclic ring formed between the two nitrogens as defined below;

TABLE 1

The following perfluoroalkylthiodialkylaminoalkyl amides and derived cationic and amphoteric derivatives can be prepared by procedures similar to those given in Examples 1 – 6.

| Ex. No. | $R_fR_1SCH_2CHR_2CONR_5D_1NR_3R_4$ — $R_f$—thiol | Dialkylaminoalkylacrylamide | $(R_fR_1SCH_2CHR_2CONR_5D_4NR_3R_4R_6)_y^+ {}_z^-I$ — Quaternizing Agent |
|---|---|---|---|
| 7 | $C_8F_{17}CH_2CH_2SH$ | $CH_2{=}CHCONHCH_2CH_2N(CH_3)_2$ | none |
| 8 | " | " | acetic acid |
| 9 | " | " | methyl iodide |
| 10 | $(CF_3)_2CFOCF_2CF_2CH_2CH_2SH$ | $CH_2{=}C(CH_3)CONH(CH_2)_3N(C_2H_5)_2$ | none |
| 11 | " | " | chloracetic acid |
| 12 | $(CF_3)_2CFO(CF_2CF_2)_2CH_2CH_2SH$ | $CH_2{=}C(CH_3)CONH(CH_2)_2N(CH_3)_2$ | none |
| 13 | " | " | 1,3-propane sultone |
| 14 | $R_fCH_2CH_2SH$ | $CH_2{=}C(CH_3)CONH(CH_2)_3N(C_4H_9)_2$ | none |
| 15 | " | " | acetic acid |
| 16 | " | " | 3-chloropropionic acid |
| 17 | $C_8F_{17}CH_2CH_2SCH_2CH_2CH_2SH$ | 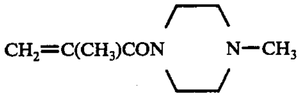 | none |
| 18 | " | " | dimethyl sulfate |
| 19 | $C_8F_{17}CH_2CH_2OCH_2CH_2CH_2SH$ | $CH_2{=}C(CH_3)CONHC_2H_4OC_2H_4N(CH_3)_2$ | acetic acid |
| 20 | " | " | diethyl sulfate |
| 21 | $C_8F_{17}CH_2CH_2N(CH_3)CH_2CH_2CH_2SH$ | $CH_2{=}C(CH_3)CONHC_2H_4(OC_3H_6)_{20}N(CH_3)_2$ | methyl chloride |

TABLE 2

| EXAMPLE NO. | SURFACE PROPERTIES OF SELECTED EXAMPLES — STRUCTURE $R_f$—$CH_2CH_2SCH(CH_3)CONH(CH_2)_3N^+(CH_3)_3\ I^-$ | CONCENTRATION .1% | .01% | .001% | .0001% |
|---|---|---|---|---|---|
| 2 | $C_8F_{17}$ | 19.3 | 33.5 | 42.7 | 59.4 |
| 4 | $^{a}R_f$ | 19.4 | 25.5 | 51.8 | 57.2 |
| 5 | $^{b}R_f$ | 22.2 | 29.5 | 48.0 | 65.1 |
| 6 | $C_8F_{17}$—$CH_2CH_2SCH_2CH(CH_3)CONH(CH_2)_3N^+(CH_3)_2C_2H_5\quad C_2H_5OSO_3^-$ | — | 21.4 | 36.5 | 67.3 |

$^{a}R_f$ Distribution $C_6$, $C_8$, $C_{10}$, $C_{12}$—40:40:13:2
$^{b}R_f$ Distribution $C_6$, $C_8$, $C_{10}$, $C_{12}$ 2:36:22:6

What is claimed is:

1. A compound having the structure $R_6$ is hydrogen or straight or branched chain alkyl of 1 to 22 carbon atoms that may also contain 1 or 2 hydroxyl groups, a free carboxylic acid group, an anionic function selected from sulfonate, sulfate, or carboxylate, or oxygen;

E is a straight or branched chain alkylene of 1 to 12 carbon atoms or alkylene polyoxyalkylene of formula $$C_mH_{2m}(OC_kH_{2k})_r$$

where

*m* is an integer of 1 to 12

*k* is an integer of 2 to 6

*r* is an integer of 1 to 40;

X is an anion selected from the group consisting of Br, Cl, I, acetate, phosphate, sulfate, methosulfate or ethosulfate;

*y* is 1 to 2, depending on the valence of X, and

*z* is 0 or 1, with the proviso that when *z* is 0, *y* is 1 and $R_6$ must be oxygen or an anionic function; if *z* is 1 $R_6$ may not be oxygen.

2. A compound of claim 1 wherein $R_2$ is hydrogen or methyl, $R_5$ is hydrogen $R_6$ is hydrogen or straight chain alkyl of 1 to 3 carbon atoms, and E is a straight chain alkylene of 2 or 3 carbon atoms or alkylene polyoxyalkylene where

*m* is an integer of 1 to 4

*k* is an integer of 2 to 4

*r* is an integer of 1 to 20.

3. A compound of claim 1 selected from the group consisting of $R_fCH_2CH_2SCH_2CHCH_3CONH(CH_2)_3N(CH_3)_2$ $(R_fCH_2CH_2SCH_2CHCH_3CONH(CH_2)_3N(CH_3)_2C_2H_5)^+C_2H_5SO_4^-$ $R_fCH_2CH_2SCH_2CHCH_3CONH(CH_2)_3N^+(CH_3)_2CH_2CO_2^-$ where $R_f$ is perfluoroalkyl of 6 to 12 carbon atoms or perfluoroalkoxyperfluoroalkyl of 4 to 12 carbon atoms.

4. A compound of claim 3 wherein $R_f$ is $(CF_3)_2CFO(CH_2CF_2)_y$ where *y* is 1 to 6.

5. The compound of claim 1 which is N-(3-Dimethylaminopropyl)-2-methyl-3-(1,1,2-tetrahydroperfluorodecanethio)-propionamide.

6. The compound of claim 1 which is 3-[2-Methyl-3-(1,1,2,2-tetrahydroperfluorodecanethio)propionamido] propyltrimethylammonium iodide.

7. The compound of claim 1 which is N-(3-Dimethylamino)propyl-2-methyl-3-(1,1,2,2-tetrahydroperfluoroalkanethio)-propionamide.

8. The compound of claim 1 which is 3-[2-methyl-3-(1,1,2,2-tetrahydroperfluorodecanethio)-propionamido] propyltrimethylammonium iodide.

9. The compound of claim 1 which is 3-[2-methyl-3-(1,1,2,2-tetrahydroperfluorodecanethio)-propionamido] propyldimethylethylammonium ethyl sulfate.

* * * * *